United States Patent
Alsop et al.

(10) Patent No.: US 12,262,984 B2
(45) Date of Patent: Apr. 1, 2025

(54) SYSTEMS AND METHODS FOR SPIN LABELING IN MAGNETIC RESONANCE IMAGING

(71) Applicant: Beth Israel Deaconess Medical Center, Inc., Boston, MA (US)

(72) Inventors: David Alsop, Newton, MA (US); Manuel Taso, Boston, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 439 days.

(21) Appl. No.: 17/756,366

(22) PCT Filed: Nov. 25, 2020

(86) PCT No.: PCT/US2020/062256
§ 371 (c)(1),
(2) Date: May 24, 2022

(87) PCT Pub. No.: WO2021/108573
PCT Pub. Date: Jun. 3, 2021

(65) Prior Publication Data
US 2023/0033905 A1  Feb. 2, 2023

Related U.S. Application Data

(60) Provisional application No. 62/940,555, filed on Nov. 26, 2019.

(51) Int. Cl.
*A61B 5/055* (2006.01)
*A61B 5/026* (2006.01)
*G01R 33/563* (2006.01)

(52) U.S. Cl.
CPC ........ *A61B 5/055* (2013.01); *G01R 33/56366* (2013.01); *A61B 5/0263* (2013.01)

(58) Field of Classification Search
CPC ..... A61B 5/055; A61B 5/0263; A61B 5/0042; A61B 5/4064; A61B 2576/026;
(Continued)

(56) References Cited

U.S. PATENT DOCUMENTS

| 7,545,142 B2 | 6/2009 | Alsop |
| 2010/0171499 A1 | 7/2010 | Sharp et al. |

(Continued)

FOREIGN PATENT DOCUMENTS

WO  WO-2018187040 A1 * 10/2018  ......... G01R 33/5602

OTHER PUBLICATIONS

Zhao, L., Vidorreta, M., Soman, S., Detre, J. A., & Alsop, D. C. (2017). Improving the robustness of pseudo-continuous arterial spin labeling to off-resonance and pulsatile flow velocity. Magnetic resonance in medicine, 78(4), 1342-1351. (Year: 2017).*
(Continued)

*Primary Examiner* — Keith M Raymond
*Assistant Examiner* — Johnathan Maynard
(74) *Attorney, Agent, or Firm* — Quarles & Brady, LLP

(57) ABSTRACT

Systems and methods are provided for producing an image of a subject using a magnetic resonance imaging (MRI) system. The method includes designing a saturation-based labeling pulse sequence for an MRI process that includes radio-frequency (RF) pulses and gradients forming a ratio of RF slice-selection gradient to time-averaged gradient that maintains multiple aliased labeling planes within an envelope of the RF pulses. The method also includes performing the MRI process to acquire image data from the subject using the saturation-based labeling pulse sequence and reconstructing a saturation-based spin labeled images of the subject using image data.

25 Claims, 6 Drawing Sheets

(58) Field of Classification Search
CPC .............. A61B 5/026; G01R 33/56366; G01R 33/5608; G01R 33/5635; G01R 33/543; G01R 33/5602; G01R 33/4833; G01R 33/4838; G01R 33/56509; G01R 33/56308; G01R 33/5616; G01R 33/54; G06T 2207/10088; G06T 7/0012; G06T 2207/30016; G06T 2207/30104
See application file for complete search history.

(56) References Cited

U.S. PATENT DOCUMENTS

| | | | | |
|---|---|---|---|---|
| 2012/0139537 | A1* | 6/2012 | Holland | G01R 33/56366 324/309 |
| 2012/0271157 | A1* | 10/2012 | Wong | A61B 5/0042 600/419 |
| 2012/0296193 | A1* | 11/2012 | Koktzoglou | A61B 5/02007 600/410 |
| 2015/0355305 | A1* | 12/2015 | Helle | G01R 33/56366 324/309 |
| 2017/0035319 | A1* | 2/2017 | Zhao | A61B 5/0263 |
| 2017/0258409 | A1 | 9/2017 | Do et al. | |
| 2019/0033412 | A1 | 1/2019 | Alsop et al. | |
| 2019/0262478 | A1 | 8/2019 | Zabow et al. | |

OTHER PUBLICATIONS

Dai, W., Garcia, D., De Bazelaire, C., & Alsop, D. C. (2008). Continuous flow-driven inversion for arterial spin labeling using pulsed radio frequency and gradient fields. Magnetic Resonance in Medicine: An Official Journal of the ISMRM, 60(6), 1488-1497 (Year: 2008).*

Garcia, D. M., De Bazelaire, C., & Alsop, D. (2005, May). Pseudo-continuous flow driven adiabatic inversion for arterial spin labeling. In Proc Int Soc Magn Reson Med (vol. 13, p. 37). (Year: 2005).*

Nair, T., Pohmann, R., & Gach, M. (2010, May). Aliasing, Off-Resonance Saturation, and Residual Signal Analysis for PCASL. In ISMRM-ESMRMB Joint Annual Meeting 2010. (Year: 2010).*

Alsop, David C., et al. "Recommended implementation of arterial spin-labeled perfusion MRI for clinical applications: a consensus of the ISMRM perfusion study group and the European consortium for ASL in dementia." Magnetic resonance in medicine 73.1 (2015): 102-116. (Year: 2015).*

Hirschler, L. (2017). Developments in preclinical arterial spin labeling (Doctoral dissertation, Université Grenoble Alpes). (Year: 2017).*

Alsop, D. et al., Reduced Transit-Time Sensitivity in Noninvasive Magnetic Resonance Imaging of Human Cerebral Blood Flow, Journal of Cerebral Blood Flow and Metabolism, 1996, 16:1236-1249.

Alsop, D. et al., Multisection Cerebral Blood Flow MR Imaging with Continuous Arterial Spin Labeling, Radiology, 1998, 208:410-416.

Alsop, D. et al. Recommended Implementation of Arterial Spin-Labeled Perfusion MRI for Clinical Applications: A Consensus of the ISMRM Perfusion Study Group and the European Consortium for ASL in Dementia, Magnetic Resonance in Medicine, 2015, 73:102-116.

Dai, W. et al., Continuous Flow-Driven Inversion for Arterial Spin Labeling Using Pulsed Radio Frequency and Gradient Fields, Magnetic Resonance in Medicine, 2008, 60:1488-1497.

Detre, J. et al., Perfusion Imaging, Magnetic Resonance in Medicine, 1992, 23:37-45.

Detre, J. et al., Perfusion Magnetic Resonance Imaging with Continuous Arterial Spin Labeling: Methods and Clinical Applications in the Central Nervous System, European Journal of Radiology, 1999, 30:115-124.

Francis, S. et al., Continuous Saturation EPI with Diffusion Weighting at 3.0 T, NMR in Biomedicine, 1999, 12 (7):440-450.

Li, L. et al., DANTE-Prepared Pulse Trains: A Novel Approach to Motion-Sensitized and Motion-Suppressed Quantitative Magnetic Resonance Imaging, Magnetic Resonance in Medicine, 2012, 68:1423-1438.

Maccotta, L. et al., The Efficiency of Adiabatic Inversion for Perfusion Imaging by Arterial Spin Labeling, NMR in Biomedicine, 1997, 10(4-5):216-221.

Nair, T. et al., Aliasing, Off-Resonance Saturation, and Residual Signal Analysis for PCASL, In ISMRM-ESMRMB Joint Annual Meeting, 2010, 1 page.

Ouyang, C. et al., Pseudo-Continuous Transfer Insensitive Labeling Technique, Magnetic Resonance in Medicine, 2011, 66:768-776.

Sardashti, M. et al., Spin-Labeling Angiography of the Carotids by Presaturation and Simplified Adiabatic Inversion, Magnetic Resonance in Medicine, 1990, 15(2):192-200.

Taso, M. et al., Off-Resonance and Flow-Velocity Immune ASL at Low-Power Using Pseudo-Continuous Saturation Labeling, Proc. Intl. Soc. Mag. Reson. Med., 2020, 28:3276, 5 pages.

Wang, J. et al., Comparison of Quantitative Perfusion Imaging Using Arterial Spin Labeling at 1.5 and 4.0 Tesla, Magnetic Resonance in Medicine, 2002, 48:242-254.

Williams, D. et al., Magnetic Resonance Imaging of Perfusion Using Spin Inversion of Arterial Water, Proc. Natl. Acad. Sci. USA, 1992, 89:212-216.

Wong, E. et al., A Theoretical and Experimental Comparison of Continuous and Pulsed Arterial Spin Labeling Techniques for Quantitative Perfusion Imaging, Magnetic Resonance in Medicine, 1998, 40(3):348-355.

Zhao, L. et al., Improving the Robustness of Pseudo Continuous Arterial Spin Labeling to Off Resonance and Pulsatile Flow Velocity, Magnetic Resonance in Medicine, 2017, 78(4):1342-1351.

PCT International Search Report and Written Opinion, PCT/US2020/062256, Apr. 12, 2021, 10 pages.

European Patent Office, Extended Search Report, Application No. 20894191.4, Nov. 17, 2023, 9 pages.

* cited by examiner

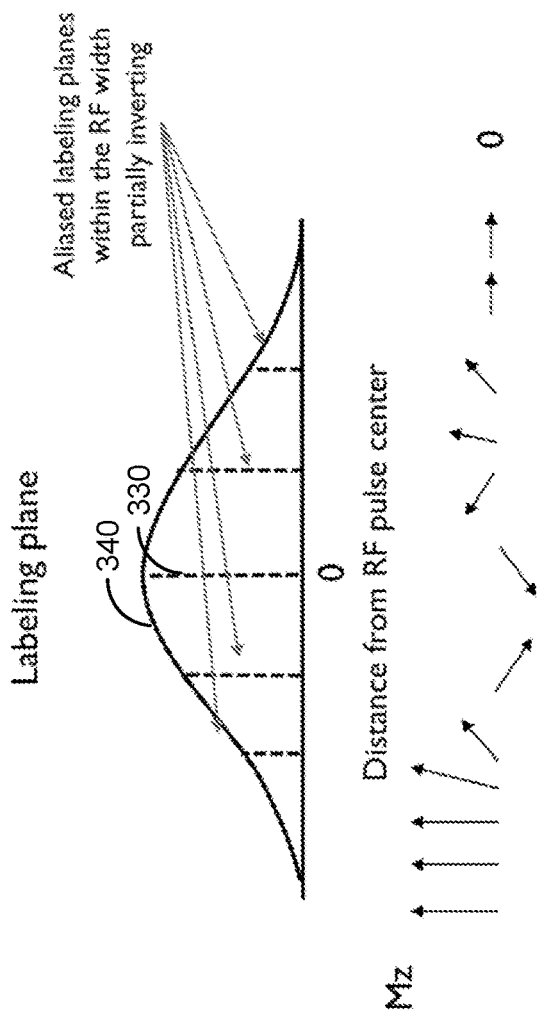
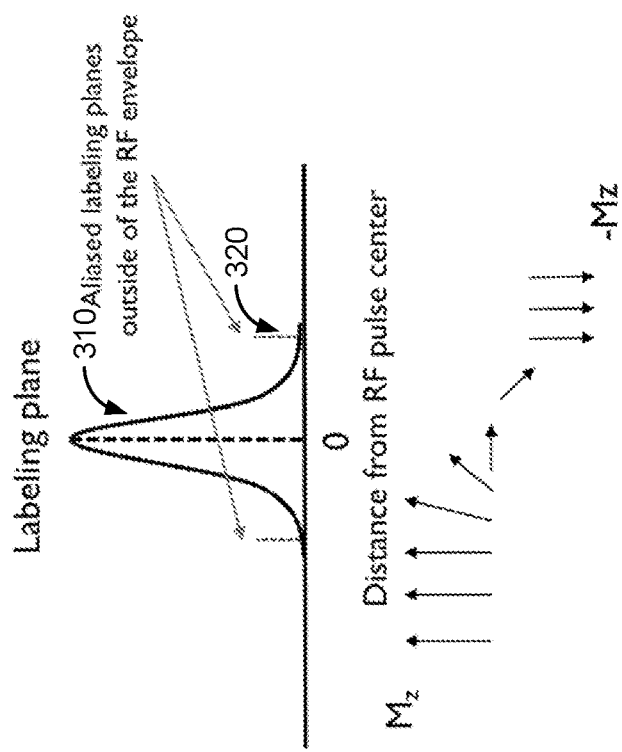
FIG. 3A
FIG. 3B

SYSTEMS AND METHODS FOR SPIN LABELING IN MAGNETIC RESONANCE IMAGING

CROSS-REFERENCE TO RELATED APPLICATIONS

The present application represents the United States national stage entry of PCI International Application Serial No. PCT/US2020/062256 filed Nov. 25, 2020, which is based on, claims priority to, and incorporates herein by reference in its entirety for all purposes, US Provisional Application Ser. No. 62/940,555, filed Nov. 26, 2019, and entitled, "SYSTEMS AND METHODS FOR SPIN LABELING MRI."

STATEMENT REGARDING FEDERALLY SPONSORED RESEARCH

N/A

BACKGROUND

Magnetic resonance imaging (MRI) is a technique used frequently in medical settings to produce images of the inside of the human body. MRI is based on detecting nuclear magnetic resonance (NMR) signals emitted by molecules under the influence of electro-magnetic fields. In particular, magnetic resonance (MR) techniques involve detecting electro-magnetic changes resulting from re-alignment of nuclear spin of molecules in the tissue of the human body. MR techniques may be used to study fluid flow, such as, for example, blood flow and/or blood perfusion in tissue. One of many possible applications is the study of blood perfusion in the human brain.

During an MRI procedure, NMR signals emitted from a volume of interest or from a slice (i.e., a relatively thin region) of the volume of interest are detected and/or otherwise acquired. The acquired NMR signals may then be reconstructed to form a two dimensional (2D) image of the slice. A plurality of such 2D images reconstructed from NMR signal data obtained from successive slices may be stacked together to form a three dimensional (3D) image. A 2D image is comprised of pixels, each pixel having an intensity (e.g., a magnitude or value) that is proportional to the strength of the NMR signal emitted by a corresponding location in the volume of interest. Similarly, a 3D image is composed of voxels, each voxel having an intensity proportional to the strength of the NMR signal emitted from a corresponding portion of the volume of interest.

As discussed above, MRI exploits the NMR phenomenon to distinguish various tissue characteristics. In particular, MRI operates by manipulating spin characteristics of tissue, and more specifically, hydrogen atoms of water molecules which compose a significant proportion of the human body, including both blood and tissue. MRI techniques include aligning the spin characteristics of hydrogen nuclei in a magnetic field, and perturbing the magnetic field with radio frequency (RF) fields.

The NMR phenomenon is invoked by the RF fields, applied at the Larmor frequency, exciting the hydrogen (or other targeted) nuclei and causing the spin to briefly precess about an axis in the direction of the applied RF signal, rather than in the direction of the applied magnetic field. The Larmor frequency is related to the rate at which a nucleus precesses about an axis, which is, in turn, proportional to the strength of the applied magnetic field. When the RF fields subsides, the spins gradually realign with the magnetic field, releasing energy in the process. The released energy may be detected and used to form one or more images representative of the hydrogen content of the tissue. The NMR signals may be detected using one or more RF coils sensitive to electromagnetic changes caused by the NMR signals. The RF coils may be the same or different than RF coils, that when driven by a signal generator, provide the RF fields used to invoke the NMR phenomenon.

Using these fundamental principles, fluid content may be measured in a variety of substances or tissue, by measuring characteristics of the tissue's NMR response. In order to detect fluid flow or perfusion in a particular region of interest, fluid flowing into that region may be "labeled" by reversing, or perturbing, the spins of the protons of the fluid in some region that is "upstream" from the region of interest, and then detecting the labeled fluid when it flows through or is perfused into the region of interest. Although terms "flow" and "perfusion" may sometimes be used interchangeably, perfusion as used herein refers to a diffusible exchange between a fluid and a substance, such as, for example, human tissue. The term "flow" as used herein, generally refers to flow of liquid in vessels, such as, for example, flow of blood in arteries. The term "labeling" refers herein to preparing nuclear spins such that, upon relaxation or recovery, a detectable NMR signal is produced.

One strategy for spin labeling includes providing RF signals that result in spin inversion for atoms exposed to the RF energy. The inversion recovery (i.e., the process of the atoms returning from the induced inverted spins) results in changes to the longitudinal magnetization that can be detected to measure blood flow and/or perfusion. Spin inversion may be achieved by generally aligning the spins in a magnetic field, and inverting the spins by applying an RF field, typically, in a direction orthogonal to the magnetic field, as discussed above. A number of RF field waveforms, referred to herein as an RF sequence, that achieve spin inversion are generally known. However, conventional RF sequences have several drawbacks, as discussed in further detail below.

By applying a gradient magnetic field to align the spins, the spin inversion effect may be localized to a particular region of interest. In particular, to achieve spin inversion, the RF field is applied at an appropriate frequency (i.e., the Larmor frequency), which depends, at least in part, on the strength of the magnetic field. Thus, an RF field applied at a particular frequency will only induce spin inversion at portions of the gradient magnetic field where the RF frequency matches the Larmor frequency at the corresponding magnetic field strength. By appropriately selecting the gradient magnetic field and RF frequency, spin inversion effects may be spatially isolated such that only spins in a region of interest are labeled.

However, despite localization efforts, magnetization transfer effects and other unrelated errors may interfere with the labeling procedure by causing more than just the atoms in the region of interest to be labeled, which in turn results in artifacts in the reconstructed images. In order to account for such effects, a control procedure may be used wherein the magnetic field gradient and RF sequence are selected to mimic the unrelated effects without invoking spin inversion. MR images reconstructed from NMR data obtained after the labeling procedure and control procedure may be used to reduce or eliminate these unwanted effects, for example, by subtracting out the effects associated with one or more control images to remove at least some of the image artifacts from the labeling images.

MR techniques in general endeavor to achieve a balance between signal to noise ratio (SNR) and power deposition. In particular, the higher the energy of the magnetic fields used (and correspondingly the higher the energy of the RF sequences needed to invoke the NMR effect), the greater the SNR of the NMR signals. Accordingly, higher energy MR results in higher contrast, better quality images. However, performing MRI at higher energies results in increased RF power deposition. There are limits to the RF power that may be deposited in the human body without harming the tissue.

Pseudo continuous arterial spin labelling (PCASL) may be performed using less RF power and generating less heat in one example of an attempt to address the aforementioned challenges. With PCASL, the goal is to achieve inversion labeling. This requires optimization of the gradient and RF pulse parameters in order to approximate flow driven adiabatic inversion. However, while pulsed radiofrequency and gradient waveforms were designed to achieve inversion of inflowing arterial spins and inversion is desirable because it provides maximized signal from labeling, there are limitations to PCASL inversion labeling.

As the RF power is reduced to meet safety requirements at 3 Tesla static magnetic fields and above, inversion efficiency can depend on flow velocity and magnetic field variations near the labeling plane, challenging extra-cranial applications, for example. At 7 Tesla, a growing high-end market for human scanning, constraints on RF power and magnetic field nonuniformity make PCASL inversion undesirable. Potential uncertainties in labeling efficiency also undermine confidence in quantification of flow with PCASL inversion, leading some to doubt the effectiveness of PCASL in applications where absolute quantification is essential. Also, although used for perfusion imaging, the flow-driven inversion labeling commonly used with PCASL presents a significant off-resonance sensitivity as well as high power deposition potentially limiting high-field applications.

Continuous saturation labeling may also be used in MRI. However, besides the lower signal resulting from saturation, saturation labeling faces challenges of detailed implementation that has essentially blocked further development. Challenges include how to effectively spoil transverse magnetization such that repeated saturation does not lead to unanticipated effects and what control sequence to use that mimics the magnetization transfer and direct saturation effects of the labeling.

Thus, there remains a need for reliable arterial spin labeled imaging while controlling RF power deposition, particularly in high-field applications.

SUMMARY OF THE DISCLOSURE

The present disclosure addresses the aforementioned drawbacks by providing systems and methods of spin labeling that balance the need for signal, while controlling power deposition, even at high field strength. In one implementation, a highly reliable continuous saturation of inflowing fluid, such as arterial blood, is provided that can use lower RF power and with greater robustness to off-resonance than traditional continuous saturation labeling techniques have achieved. In some configurations, a pseudo continuous arterial spin labelling (PCASL) pulse sequence and imaging process is provided that facilitates consistent and continuous saturation of inflowing fluid. Using saturation instead of inversion in a PCASL method consistent with the systems and methods provided herein can reduce power and provide for higher certainty of efficiency.

In one configuration, a method is provided for producing an image of a subject using a magnetic resonance imaging (MRI) system. The method includes designing a saturation-based labeling pulse sequence for an MRI process that includes radio-frequency (RF) pulses and gradients forming a ratio of RF slice-selection gradient to time-averaged gradient that maintains multiple aliased labeling planes within an envelope of the RF pulses. The method also includes performing the MRI process to acquire image data from the subject using the saturation-based labeling pulse sequence and reconstructing a saturation-based spin labeled images of the subject using image data.

In one configuration, a method is provided for producing a perfusion image of a subject using a magnetic resonance imaging (MRI) system. The method includes determining a slice profile for a spin labeling perfusion imaging sequence. The method also includes determining a ratio of a radio frequency (RF) slice selection gradient to a time averaged gradient for the spin labeling perfusion imaging sequence and reducing the ratio so a plurality of aliased labeling planes are within the slice profile. The method also includes acquiring perfusion image data of the subject from tissue regions downstream of the plurality of aliased labeling planes. A spin labeled perfusion image of the subject may then be reconstructed from the acquired perfusion image data.

In one configuration, a system is provided for producing a perfusion image of a subject using a magnetic resonance imaging (MRI) system. The system includes a computer system configured to: i) determine a slice profile for a spin labeling perfusion imaging sequence; ii) determine a ratio of a radio frequency (RF) slice selection gradient to a time averaged gradient for the spin labeling perfusion imaging sequence; iii) reduce the ratio so a plurality of aliased labeling planes are within the slice profile; iv) acquire perfusion image data of the subject from the plurality of aliased labeling planes; and v) reconstruct a spin labeled perfusion image of the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 3A is a graph of a non-limiting example PCASL Inversion where aliased labeling planes are outside of the RF envelope.

FIG. 3B is a graph of a non-limiting example PCASL saturation where aliased labeling planes are within the RF envelope.

DETAILED DESCRIPTION

Systems and methods are provided for a pseudo-continuous saturation based labeling strategy for low SAR robust perfusion imaging. The systems and methods may be used to achieve reliable continuous saturation of inflowing fluid, such as arterial blood, that can be performed at lower RF powers and with greater robustness to off-resonance. In some configurations, a pseudo continuous arterial spin labelling (PCASL) method may be performed using saturation instead of inversion, which may reduce power and provide for higher certainty of efficiency. A labeling scheme may be used that takes advantage of multiple aliased labeling planes that arise within the labeling RF envelope when reducing the peak-to-average gradient ratio.

Reduced power and higher certainty of efficiency may be beneficial in numerous applications, even at the potential expense of signal to noise ratio (SNR). Such applications may include: arterial spin labelling (ASL) at 7 Tesla and higher; as a low resolution prescan with better quantification to serve as a reference to optimize PCASL inversion or to adjust absolute numbers of a PCASL inversion sequence; for use in patients with limitations on deposited RF power because of implants or other contraindication to higher power; when longer labeling is desirable but power constraints at 3 Tesla or above limit the achievable labeling; in body applications where the range of velocities is higher and RF and magnetic field spatial variations are higher such as with free-breathing acquisitions; in applications where tortuosity of arterial vessels makes inversion PCASL inefficient or potentially inefficient; and the like.

Figure 1:
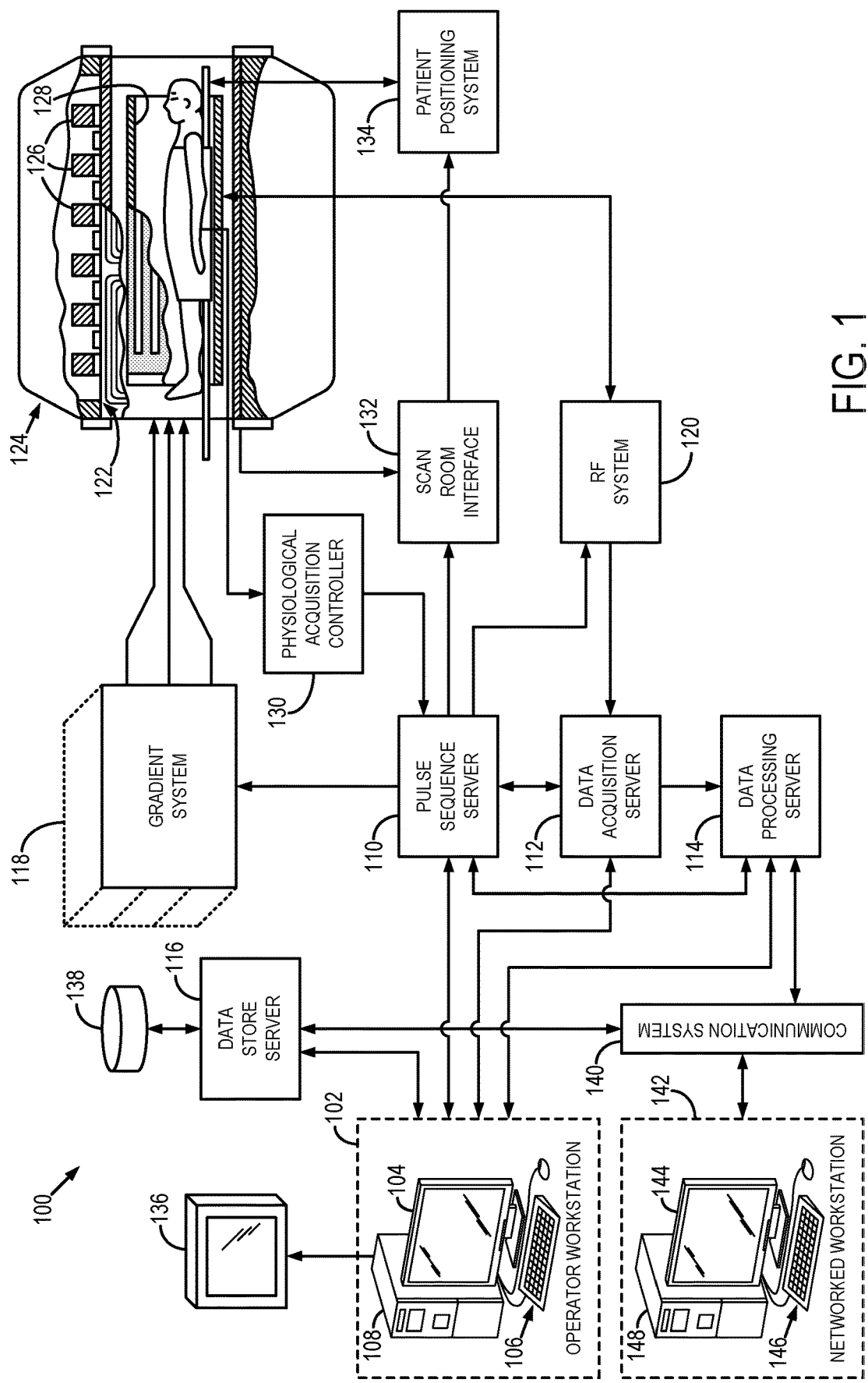
FIG. 1 is a schematic of a non-limiting example MRI system that can implement the methods according to the present disclosure.

Referring particularly now to FIG. 1, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 110 may receive patient data from a physiological acquisition controller 130. By way of example, the physiological acquisition controller 130 may receive signals from a number of different sensors connected to the patient, including electrocardiograma) signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

Figure 2:
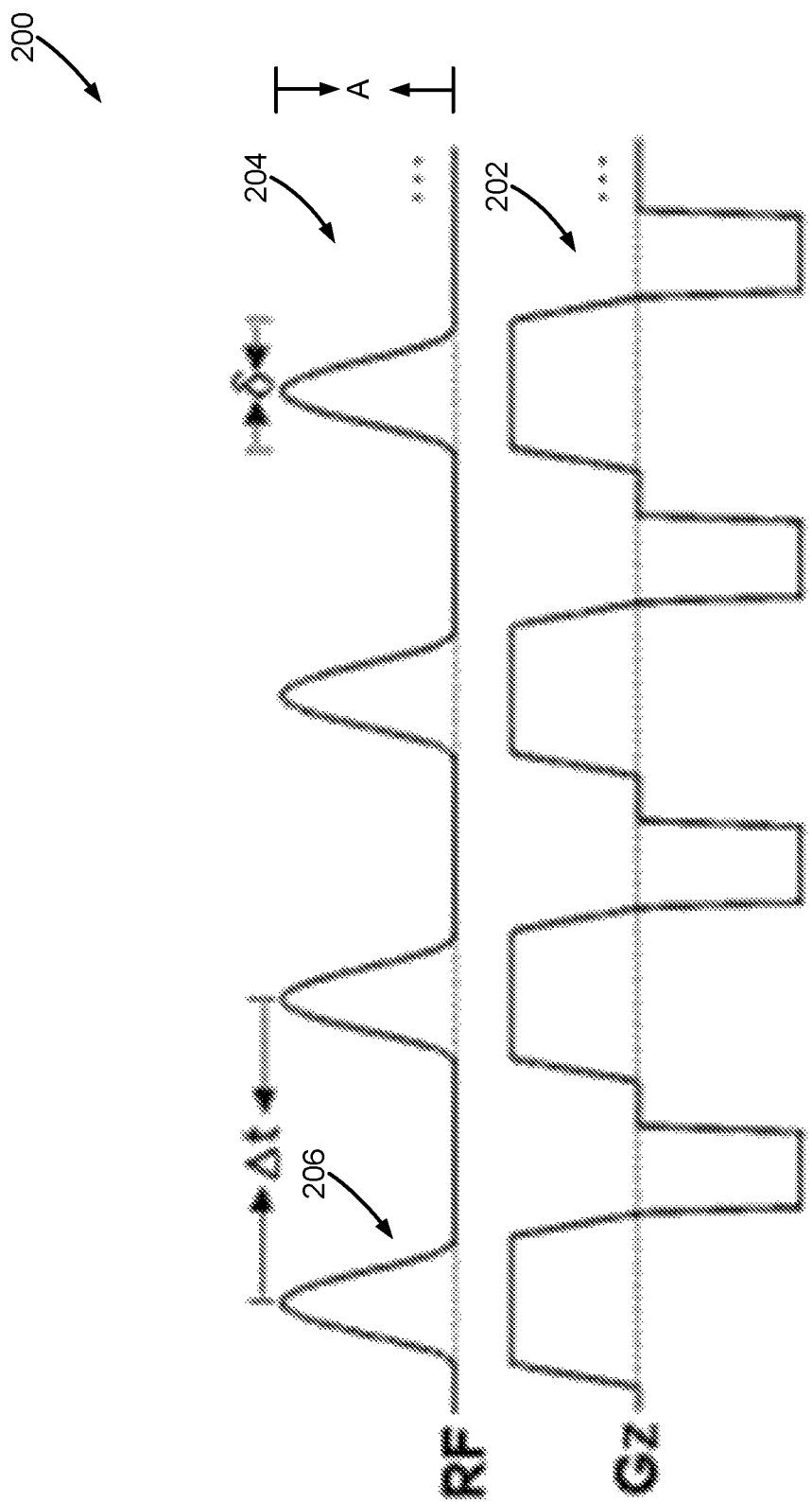
FIG. 2 is a graph of a non-limiting example PCASL labeling sequence.

Referring to FIG. 2, a non-limiting example schematic of one labeling sequence 200 in accordance with the present disclosure is shown. In particular, the sequence 200 forms a PCASL inversion module. The parameters and objectives of the PCASL inversion module may be selected for saturation with a similar sequence timing to an inversion PCASL.

In one configuration, amplitude of a PCASL gradient 202 and, correspondingly and importantly, the amplitude (A) of RF pulses 204 and/or the phases of the RF pulses may be selected to achieve saturation of spins in a target region. For example, a series of repeated, short pulses may be used to achieve saturation. This may enable the use of a control where the gradients 202 are fully refocused and the RF pulses 204 are alternated in sign. It is surprising that modification of amplitudes (A) can achieve saturation rather than inversion. This can be traced to the inclusion of multiple inversion planes within the RF envelope 206 formed between the peak of the RF pulse ($\delta$) as the amplitude declines and before the subsequent RF pulse over the time ($\Delta t$) between pulses. Because saturation may be achieved by repeated (even inefficient) inversion, the resulting saturation is largely independent of RF amplitude (A). It also can be achieved with much lower amplitude (A) than would be required using inversion pulses, which substantially reduces required power and increases reliability.

Referring to FIG. 3A, a PCASL inversion is shown where aliased labeling planes 310 may be seen outside 320 of the RF envelope 310. When PCASL is configured, or even optimized, for inversion labeling, the gradients and RF pulses are designed to create one inversion plane within the RF pulse width while aliased inversion planes are outside the pulse width or envelope 310. Off-resonance sensitivity arises in PCASL inversion because it induces shifts of the labeling plane away from the center (at point 0) of the pulse where RF power is lower.

Referring to FIG. 3B, a non-limiting example PCASL saturation is shown where aliased labeling planes 330 may be seen within the RF envelope 340. For saturation labeling, the ratio of the RF slice selection gradient to the time averaged gradient may be reduced such that multiple aliased labeling planes 330 are within the slice profile or envelope 340. This introduces multiple, partially efficient "inversions" that ultimately lead to saturation of flowing spins. Off-resonance sensitivity may be greatly reduced relative to inversion because it shifts the multiple lines around within the pulse envelope 340. The unbalanced gradient control, such as that used in PCASL inversion, also serves as an effective control for saturation.

That is, during design or optimization of a pulse sequence in accordance with the present disclosure, the ratio of the RF slice selection gradient to the time averaged gradient can be advantageously managed. For example, the present disclosure advantageously and surprisingly recognizes that, if the RF envelope is too spatially narrow, then even if there are many planes, they will not achieve saturation. So instead, the RF envelope is designed to be spatially wider than in inversion PCASL. But if the labeling planes are too close together, then the labeling planes are in the transition region of the RF pulse. In one non-limiting example, sharper RF envelopes can be utilized by using different RF pulses with different slice profiles to increase the sharpness of the transition region, while also adjusting the ratio of the RF slice selection gradient to the time averaged gradient, or other metrics that facilitate keeping the multiple aliased labeling planes 330 within the slice profile or envelope 340. Irrespective of the tools used to control the RF pulses and/or the metric used to assess design parameters, the shape of the RF envelope and the number of aliased labeling planes within it can be selected or even optimized based on priorities for labeling robustness, power deposition, and elimination of residual effects of the RF on downstream tissues (i.e., tissues located such that the labeled spins flow "down" into the tissues from which data acquisition is performed).

Figure 4:
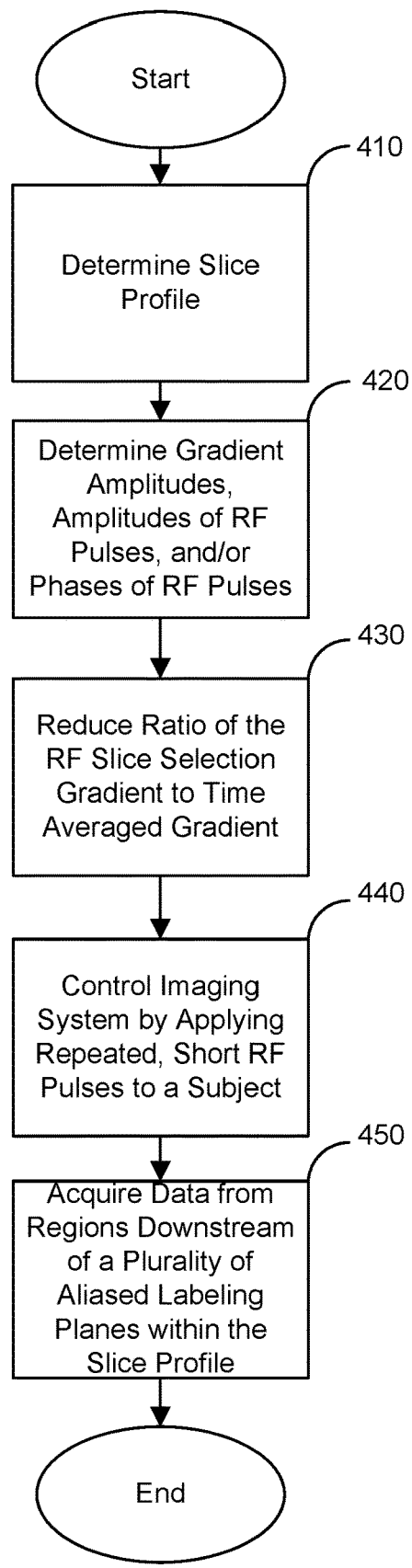
FIG. 4 is a flowchart depicting non-limiting example steps for performing a saturation imaging method according to the present disclosure.

Referring to FIG. 4, non-limiting example steps for performing a PCASL saturation are shown. A slice profile may be determined at step 410. Gradient amplitudes, and/or amplitudes of RF pulses, and/or phases of RF pulses may be determined at step 420. A ratio of RF slice selection gradient to time averaged gradient may be reduced at step 430 such that a plurality of aliased labeling planes may be within the slice profile. An imaging system may be controlled by applying repeated, short RF pulses to a subject at step 440. Data is acquired from regions downstream of the plurality of aliased labeling planes within the slice profile, such as depicted in FIG. 3B, may be acquired at step 450 using a magnetic resonance imaging system.

Non-Limiting Example Simulation

Labeling efficiency was simulated using a numerical integration of Bloch equations. Efficiency was simulated over a range of average power (B) from 0.2 to 1.5 µT and peak-to-average gradient ratio from R=1 to 7 by 0.5 steps with an average gradient set at 0.5 mT/m (to avoid being close to background gradients levels) at a fixed flow-velocity of 50 cm/s for a Hann-shaped pulse of 500 us played every 1 ms or shorter when hardware compatible.

Non-Limiting Example Experiment

Three volunteers were scanned at 3T using 32-ch coils for brain (N=1) and kidney (N=2) imaging. A single-slice single-shot FSE was acquired, positioned axial mid-ventricles for the brain and mid-kidneys coronal. SSFSE parameters were TR/TE=6000/40 ms,mtx=128,rBW=20.83 kHz, 7-mm thick slice, flip-angle=120°. Two datasets were acquired in each case with either the recommended optimized inversion scheme (B=1.4 µT,R=7,G=0.5 mT/m) and the proposed saturation scheme (B=0.75 µT,R=2,G=0.5 mT/m) with a background-suppressed (BS) PCASL preparation using a w=1.5 s labeling and a single PLD=1.5 s (kidney) and 2 s (brain), with 14 pairs for the brain and 7 for the kidneys. Kidney acquisitions were acquired with a timed-breathing strategy.

Image reconstruction was performed offline, with a complex ASL subtraction followed by homodyne reconstruction. Absolute cerebral and renal blood-flows (f) were quantified using a 1-compartment model, such as eq (3) below.

$$f = \frac{[6000 \cdot \lambda \cdot dM \cdot \exp(PLD/T_{1b})]}{[IF \cdot \alpha \cdot T_{1b} \cdot M_0 \cdot \exp(-w/T_{1b})]} \quad (3)$$

With IF=1 for the saturation-based and 2 for the inversion-based labeling strategies. The labeling efficiency a was estimated at 0.6 for PCASL-I (0.8×0.75 for BS) and 0.8 for PCASL-S because of BS. A mean SNR was calculated for both labeling schemes and a ratio of PCASL-I/PCASL-S.

Non-Limiting Example Results

Figure 5:
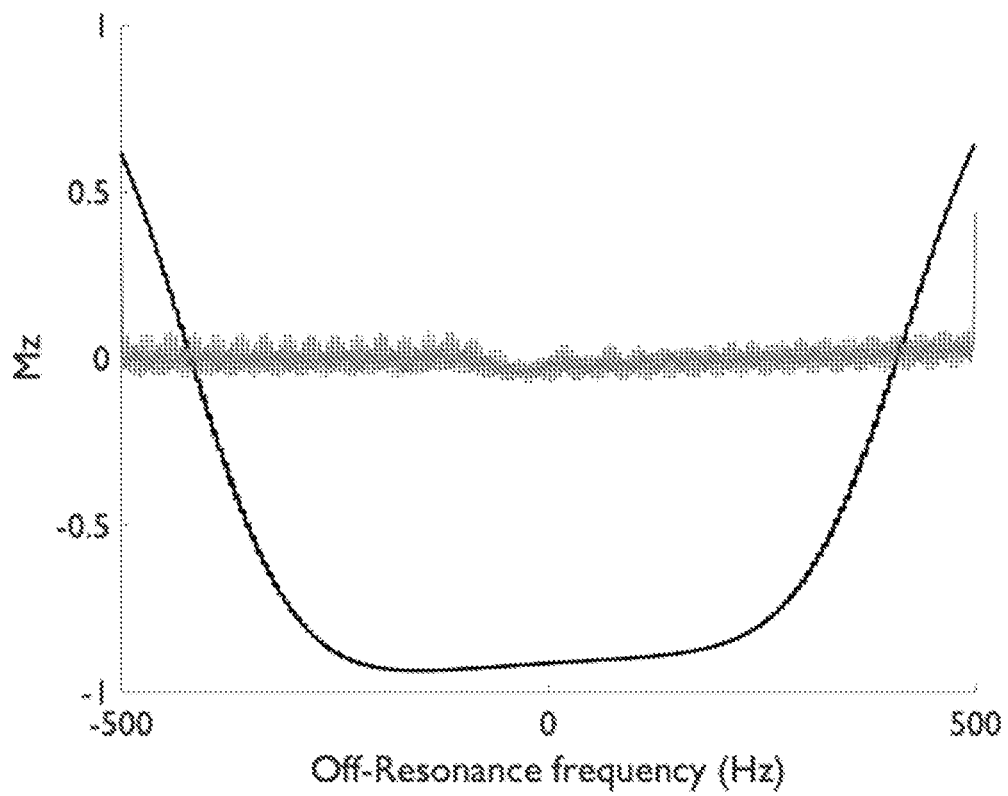
FIG. 5 is a graph of non-limiting example labeling efficiency for a range of off-resonance frequencies for a typical PCASL inversion and a saturation method according to the present disclosure.

Referring to FIG. 5, non-limiting example labeling efficiency for a range of off-resonance frequencies for a typical PCASL inversion (black) and a saturation scheme (red) according to the present disclosure are shown. Non-limiting example simulation results showed that by reducing the average B (0.75 µT) with a low gradient ratio (2), it is possible to obtain a flat efficiency of 0 corresponding to spins saturation over a wide-range of off-resonance frequencies compared to optimized PCASL inversion labeling.

Figure 6:
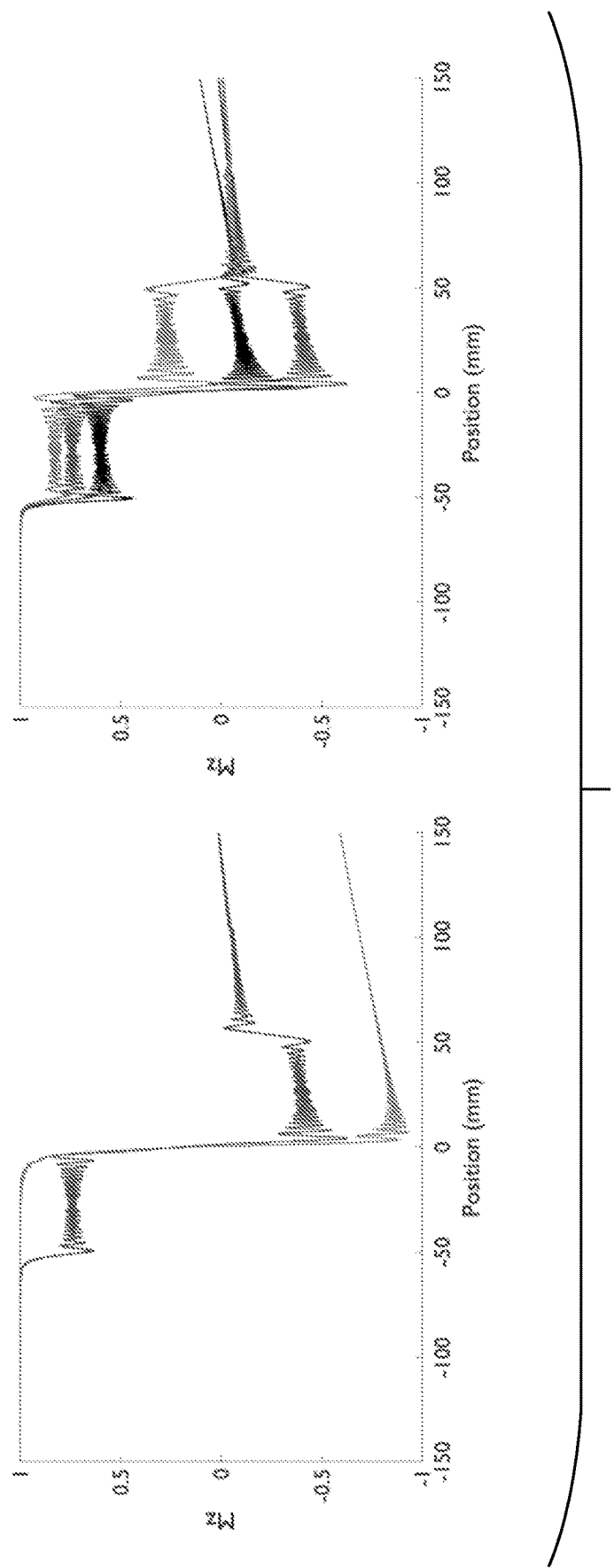
FIG. 6. is a graph of non-limiting example results for Mz spatial profiles for inversion and saturation, and effect of spin velocities on efficiency.

Referring to FIG. 6, non-limiting example results are shown for Mz spatial profiles (left) for inversion (red) and saturation (blue) highlighting effects of multiple aliased labeling planes on resulting longitudinal magnetization leading to effective spin saturations for a single velocity of v=50 cm/s and (Right) effect of spin velocities on efficiency for v=30 cm/s (black), 50 cm/s (blue) and 70 cm/s (red). Saturation was achieved with B=0.75 µT, G=0.5 mT/m, R=2. When looking at the spatial profile of longitudinal magnetization, multiple labeling planes appear within the Hann-pulse envelope eventually leading to spins saturation, but also that this strategy is robust across a range of flow velocities.

A lower SNR was measured using the PCASL-S vs I (21.0vs36.9) in the kidney scan but the difference in SNR was not marked in the brain (16vs15). A reduction in ASL signal fluctuation was observed across repetitions from 6 to 4% in the brain (STD % of the mean perfusion signal) but more significant in the kidney case from 26 to 18%, suggesting increased labeling temporal stability. Additionally, a marked reduction of SAR from 2 to 1.1 W/kg for the kidney and 1.7 to 0.9 W/kg for the brain was seen.

Numbers consistent with healthy renal flow were observed while markedly reducing in-ROI STD in the renal cortex in the saturation case (261±80 vs 224±40 mL/100/min). In the brain, similar observations were made (80±20 vs 61±15 mL/100 g/min).

Non-limiting example results show that saturation-based labeling strategies based on a minor modification of PCASL can lead to an off-resonance robust labeling while greatly reducing power deposition, which may be used for ultra-high-field robust ASL perfusion imaging. Saturation labeling also facilitates ASL quantification by reducing the influence of labeling efficiency on estimated blood-flow by rendering it much more insensitive to off-resonance.

In some configurations, the systems and methods of the present disclosure may be included as a replacement or option on existing software implementations of arterial spin labeling on clinical scanners. In some configurations, the systems and methods may provide for extension of arterial spin labeling to high field scanners (7 Tesla), where the technique has not been reliably implemented. The systems and methods may also be desirable for use on animal scanners where the limited requirements for field uniformity may make it desirable on these typically higher field strength scanners.

The present disclosure has described one or more preferred embodiments, and it should be appreciated that many equivalents, alternatives, variations, and modifications, aside from those expressly stated, are possible and within the scope of the invention.

The invention claimed is:

1. A method for producing an image of a subject using a magnetic resonance imaging (MRI) system, the steps comprising:
    a) designing a saturation-based labeling pulse sequence for an MRI process that includes radio-frequency (RF) pulses and gradients forming a ratio of RF slice-selection gradient to time-averaged gradient that maintains multiple aliased labeling planes within an envelope of the RF pulses;
    b) performing the MRI process to acquire image data from the subject using the saturation-based labeling pulse sequence; and
    c) reconstructing a saturation-based spin labeled images of the subject using image data.

2. The method of claim 1, wherein the RF pulses have a flip angle of less than 90 degrees.

3. The method of claim 1, wherein the saturation-based labeling pulse sequence includes a fully balanced control sequence.

4. The method of claim 1, wherein the saturation-based labeling pulse sequence forms a pseudo-continuous arterial spin labelling (PCASL) pulse sequence.

5. The method of claim 4, wherein designing the saturation-based labeling pulse sequence includes adjusting at least one of an amplitude of the gradients, an amplitude of the RF pulses, or a phase of the RF pulses using the ratio to maintain the multiple aliased labeling planes within an envelope of the RF pulses.

6. The method of claim 1, wherein the RF pulses alternate in sign.

7. The method of claim 1, wherein the saturation-based labeling pulse sequence includes an arterial spin labeling pulse sequence.

8. The method of claim 1, wherein designing the saturation-based labeling pulse sequence includes selecting at least one of an amplitude of the gradients, an amplitude of the RF pulses, or a phase of the RF pulses to control at least one of off-resonance effects or power deposition during the MRI process.

9. The method of claim 1, wherein the MRI system includes a high-field MRI system with field strength greater than or equal to 3 T.

10. A method for producing an image of a subject using a magnetic resonance imaging (MRI) system, the steps comprising:
    a) determining a slice profile for a spin labeling imaging pulse sequence;
    b) determining a ratio of a radio frequency (RF) slice selection gradient to a time averaged gradient for the spin labeling perfusion imaging sequence;
    c) reducing the ratio so that a plurality of aliased labeling planes are within the slice profile;
    d) acquiring image data of the subject from regions downstream of the plurality of aliased labeling planes using a pulse sequence designed from steps a) through c); and
    e) reconstructing an image of the subject from the image data acquired at step d).

11. The method of claim 10, wherein the pulse sequence includes a pseudo continuous arterial spin labelling (PCASL) pulse sequence.

12. The method of claim 11, wherein step c) further includes adjusting at least one of an amplitude of a PCASL gradient, an amplitude of an RF pulse, or a phase of the RF pulse to generate saturation-based labeling.

13. The method of claim 11, further comprising using repeated, RF pulses selected to generate saturation-based labeling.

14. The method of claim 13, wherein the repeated RF pulses are alternated in sign.

15. The method of claim 10, wherein the spin labeling includes arterial spin labeling.

16. The method of claim 10, wherein step c) further includes reducing at least one of off-resonance effects or power deposition.

17. The method of claim 10, wherein the MRI system includes a high-field MRI system with field strength greater than or equal to 3 T.

18. A magnetic resonance imaging (MRI) system for producing an image of a subject, comprising:
    a) a computer system configured to:
        i) determine a slice profile for a radio frequency (RF) pulse of a spin labeling imaging sequence;
        ii) determine a ratio of an RF slice selection gradient to a time averaged gradient for the spin labeling perfusion imaging sequence;
        iii) reduce the ratio so that a plurality of aliased labeling planes are within the slice profile;
        iv) acquire perfusion image data of the subject from tissue regions downstream of the plurality of aliased labeling planes; and
        V) reconstruct a spin labeled perfusion image of the subject.

19. The system of claim 18, wherein the imaging sequence is a pseudo continuous arterial spin labelling (PCASL) sequence.

20. The system of claim 19, wherein the computer system is further configured to adjust at least one of an amplitude of a PCASL gradient, an amplitude of an RF pulse, or a phase of the RF pulse to generate saturation-based labeling.

21. The system of claim 19, wherein the computer system is further configured to use repeated, short RF pulses to generate saturation-based labeling.

22. The system of claim 21, wherein the repeated RF pulses are alternated in sign.

23. The system of claim 18, wherein the spin labeling includes arterial spin labeling.

24. The system of claim 18, wherein at least one of off-resonance effects or power deposition are reduced.

25. The system of claim 18, wherein the MRI system includes a high-field MRI system with field strength greater than or equal to 3T.

* * * * *